United States Patent [19]
Meyer et al.

[11] Patent Number: 5,599,556
[45] Date of Patent: Feb. 4, 1997

[54] PROLAMINE COATINGS FOR TASTE MASKING

[75] Inventors: Glenn A. Meyer, Waukegan, Ill.; Terrence B. Mazer, Reynoldsburg, Ohio

[73] Assignee: Abbott Laboratories, Abbott Park, Ill.

[21] Appl. No.: 245,927

[22] Filed: May 19, 1994

Related U.S. Application Data

[63] Continuation-in-part of Ser. No. 23,301, Feb. 26, 1993, abandoned, which is a continuation-in-part of Ser. No. 815,458, Dec. 31, 1991, abandoned.

[51] Int. Cl.⁶ ..................................... A61K 9/14
[52] U.S. Cl. ................ 424/491; 424/490; 424/498; 424/439; 424/408
[58] Field of Search .................. 424/452, 460, 424/491, 498

[56] References Cited

U.S. PATENT DOCUMENTS

| | | | |
|---|---|---|---|
| 3,351,531 | 11/1967 | Noznick et al. | 424/491 |
| 3,497,369 | 2/1970 | Martin | 106/153 |
| 3,802,896 | 4/1974 | Westall et al. | 523/100 |
| 4,079,131 | 3/1978 | Lin et al. | 514/197 |
| 4,137,300 | 1/1979 | Sheth et al. | 424/460 |
| 4,332,790 | 6/1982 | Sozzi et al. | 424/498 |
| 4,384,004 | 5/1983 | Cea et al. | 426/3 |
| 4,418,084 | 11/1983 | Murray et al. | 426/250 |
| 4,433,076 | 2/1984 | Bauer et al. | 523/342 |
| 4,661,359 | 4/1987 | Seaborne et al. | 426/89 |
| 4,749,575 | 1/1988 | Rotman | 424/441 |
| 4,800,087 | 1/1989 | Mehta | 424/497 |
| 4,876,094 | 10/1989 | Benton et al. | 424/491 |
| 4,876,097 | 10/1989 | Autant et al. | 426/74 |
| 4,931,295 | 6/1990 | Courtright et al. | 426/5 |
| 5,077,053 | 12/1991 | Kuncewitch et al. | 424/441 |
| 5,085,868 | 2/1992 | Mattson et al. | 424/490 |
| 5,098,718 | 3/1992 | Ardaillon et al. | 426/2 |

FOREIGN PATENT DOCUMENTS

| | | |
|---|---|---|
| 188953 | 7/1986 | European Pat. Off. . |
| 1323056 | 2/1963 | France . |
| 6275 | 9/1968 | France . |
| 45-12759 | 11/1970 | Japan . |
| 760403 | 10/1956 | United Kingdom . |
| 91/06227 | 5/1991 | WIPO . |

OTHER PUBLICATIONS

Gennadios et al., "Edible Films and Coatings from Wheat and Corn Proteins", Food Techology, Oct. 1990, pp. 63–69.

*Primary Examiner*—Neil Levy
*Attorney, Agent, or Firm*—L. R. Drayer; D. O. Nickey; T. D. Brainard

[57] ABSTRACT

Prolamine fractions of grain proteins, applied as a single coating in weight ratios of 5 to 100% relative to the active substance being coated, result in the production of a liquid suspension which effectively masks the taste of orally administered drugs which often are extremely bitter. The taste masking is stable over prolonged periods of storage time of the suspension. The prolamine coating does not restrict the immediate bioavailability of the active substance. Prolamine coating is effective in masking the taste of antibiotics, vitamins, dietary fiber, analgesics, enzymes and hormones. Zein, gliadin or a mixture thereof, particularly in combination with between 2.5 and 15% of a water insoluble vegetable source oil or a wax capable of plasticizing the prolamine fraction, when applied to particles of drugs or nutritional supplements, to an effective thickness of about 1 to about 35 micrometers, are particularly effective in preventing the release of the active substance from the encapsulated particle and also in masking the unpleasant taste of the coated active substance.

10 Claims, 3 Drawing Sheets

PROLAMINE COATINGS FOR TASTE MASKING

This application is a continuation-in-part of U.S. patent application Ser. No. 08/023,301 filed Feb. 26, 1993, now abandoned, which is a continuation of part of U.S. patent application Ser. No. 07/815,458 filed Dec. 31, 1991, now abandoned.

TECHNICAL FIELD

This invention relates to oral formulations which effectively mask the unpleasant taste of drugs, such as antibiotics or benzodiazepines, or nutritionals such as dietary fiber or amino acid supplements, and other similar pharmaceuticals or nutritional supplements with bitter or otherwise undesirable taste characteristics. More specifically, the invention relates to a single-coat taste-masking formulation which encapsulates said pharmaceuticals or nutritional supplements. More particularly, this invention relates to and discloses liquid suspensions of single coated dosage forms that mask the unpleasant taste of the encapsulated agent, said suspensions retaining their taste masking capacity, i.e. remain stable, even though dispersed in a liquid medium for a significant period of time prior to use. Further, said liquid suspensions may be swallowed without producing a bitter taste in the mouth, but the encapsulated agent is immediately bioavailable upon exposure to the pH levels found in the stomach.

BACKGROUND OF THE INVENTION

Oral administration of pharmaceuticals and nutritionals is one of the most popular methods of delivery of such beneficial agents. Liquid suspension dosage forms are a preferred route of such oral administration for both children and adults who have difficulty swallowing capsules or tablets. Furthermore, infants cannot be given tablets or capsules. Palatability of the ingested material is an extremely important factor in ensuring the likelihood that the recipient will ingest the pharmaceutical or nutritional. Accordingly, masking of the unpleasant taste characteristics of the pharmaceutical or nutritional is an important factor in the formulation of these agents. Further, the stability of the liquid suspension is an extremely important factor. As used herein and in the claims the term "stability" means the ability of the liquid suspension to mask the unpleasant taste of the encapsulated material for a significant period of time prior to ingestion. In other words, use of the claimed composition results in minimal leakage of the active substance into the suspending medium. Additionally, after ingesting the pharmaceutical or nutritional supplement, it is often times desirable for the nutritional or pharmaceutical to be immediately available to the person in need of same.

Because of the strong, unpleasant taste of many pharmaceuticals or nutritional supplements, flavorings, either alone or in combination with sweeteners and other additives, have been employed to improve taste and palatability. The formulation of a pleasant-tasting and palatable product through the sole use of flavorings, sweeteners and additives, however, has been unsuccessful when using beneficial agents which have a particular bitter taste, such as the macrolide family of antibiotics, in particular erythromycin and clarithromycin. Attempts have been made to formulate these antibiotics into suspension dosage forms or into taste-masked chewable tablets using known coating or encapsulation processes with very limited success.

Japanese Kokoku Shu 45-12759, published Nov. 1, 1967, teaches that a mixture of 90–99% zein and 1–20% hydroxypropylmethylcellulose (HPMC) may be used to coat tablets for taste and odor masking. The application employs the high molecular weight polymeric HPMC component (exemplified at levels of 10% and above) for its film-forming properties, in a coating used to prevent the disintegration of Vitamin C as measured by temperature and time. This reference teaches that HPMC must be mixed with zein to obtain taste masking properties.

U.S. Pat. No. 3,939,259, issued Feb. 17, 1976, employed prolamine from corn grain protein (i.e. zein), with approximately an equal level of shellac and a lesser amount of ethylcellulose, to coat digitoxin particles, but did so in an attempt to achieve a sustained release effect. Since the incorporation of ethylcellulose may interfere with absorption of the active agent in a timely manner, its incorporation into the composition of the present invention for an immediately available agent would be unsuitable.

U.S. Pat. No. 4,384,004, issued on May 17, 1983, discloses the encapsulation of the artificial sweetener, L-aspartyl-L-phenylalanine methyl ester, with additional coating materials, which may include zein, for increasing shelf life stability.

U.S. Pat. No. 5,098,718, issued on Mar. 24, 1992, discloses a coating composition, consisting of very broad ranges of zein, a hydrophobic substance, an inorganic filler and an optional filler and an optional non-water soluble polymer, for coating feed additives which are intended for ruminants. The coating composition claimed in this patent is stable in the rumen and not substantially degraded in the abomasum of a ruminant, but is primarily degraded by the enzymes present in the small intestines of a ruminant. This delayed release would also be a problem when immediate bioavailability is desired.

U.S. Pat. No. 5,160,742, issued on Nov. 3, 1992, discloses a dual coating composition for sustained delivery of an active substance, said composition comprising at least a coating of prolamine and an enteric compound.

In comparison with these known formulations, the present invention provides a simple, inexpensive taste-masked stable product in suspension, while providing immediate bioavailability. This taste masking ability, without delaying release of the beneficial agent, is realized with a single coating layer of a simple, inexpensive formulation consisting predominantly of a prolamine fraction of grain, with low to moderate molecular weight plasticizer needed to form the film coating.

SUMMARY OF THE INVENTION

The present invention is directed to an orally-administerable composition comprising: (a) a core mixture of a pharmaceutically active agent or a nutritional supplement, having a surface; and (b) a single outer polymeric coating layer comprising a prolamine fraction of grain protein, preferably zein or gliadin or mixtures thereof, and a low-to-moderate weight nonpolymeric agent for plasticizing said prolamine, preferably a vegetable source water insoluble oil or wax, wherein by weight the ratio of prolamine to plasticizing agent is from 40:1 to 4:1, preferably 20:1 to 20:3.

The present invention further relates to a composition wherein by weight the ratio of the pharmaceutically effective agent or nutritional to the prolamine fraction is 20:1 to 1:1, and the single outer layer is from 1 to about 35 micrometers thick. In particular, the invention comprises a stable taste-masking liquid suspension capable of being ingested without producing the unpleasant taste associated with the active agent, while still providing immediate bioavailability upon exposure to the pH levels found in the stomach of a human. The taste masking property of the claimed composition is stable in that such compositions are able to mask the unpleasant taste of the encapsulated active agent for a substantial period of time when stored as a liquid suspension, i.e., minimal leakage of the active agent from the encapsulated core occurs during storage.

Figure 1:
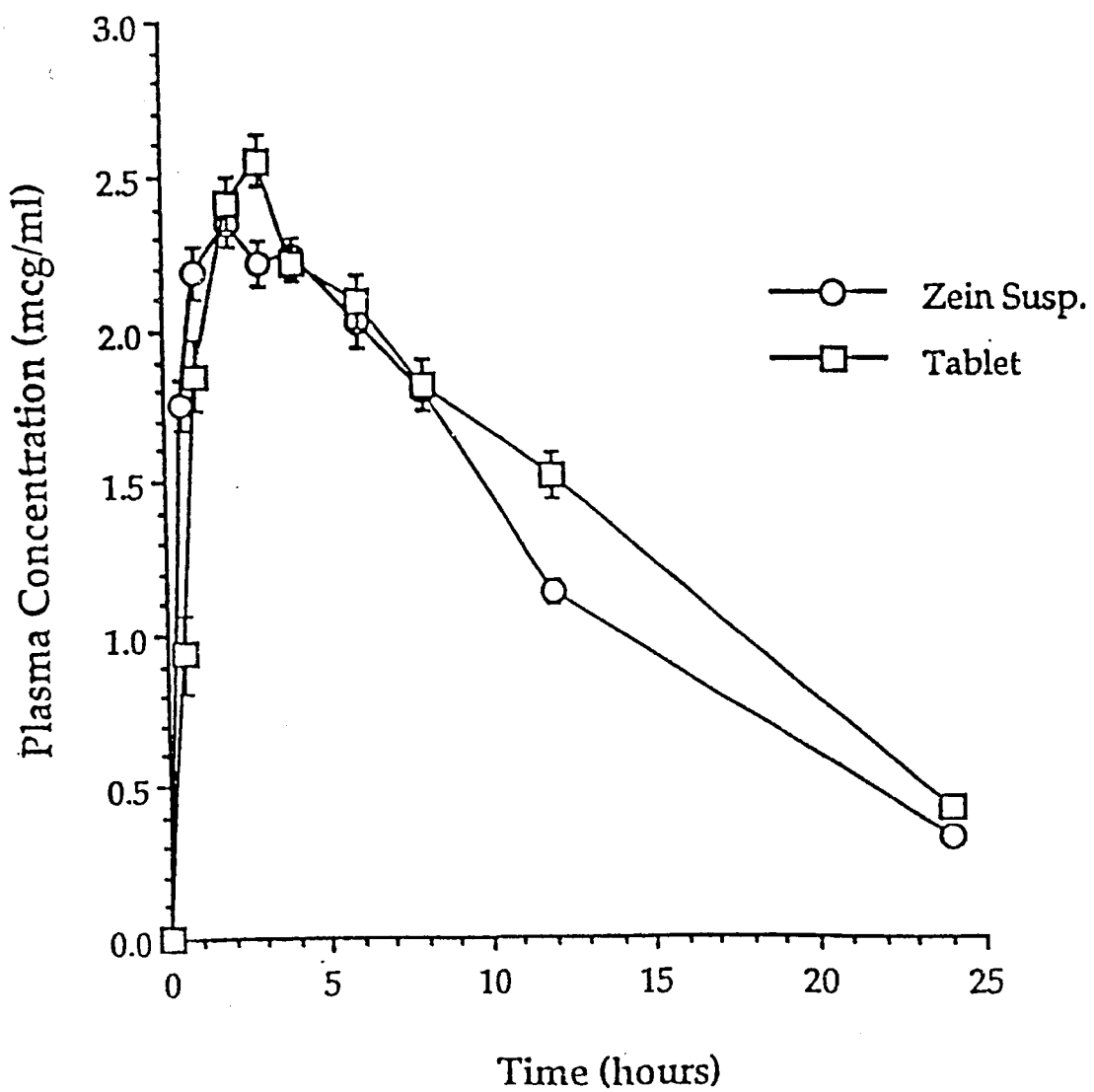
FIG. 1 is a graph of the plasma concentration versus time of both a zein coated clarithromycin suspension and an uncoated clarithromycin tablet reference (control), administered at 125 mg of clarithromycin activity per dog. This graph illustrates the bioavailability of the claimed composition.

DETAILED DESCRIPTION OF THE INVENTION.

The present invention relates to the use of a single outer polymeric coating layer to encapsulate and thereby effectively and stably mask the taste of pharmaceutically active agents or nutritional supplements which have bitter or otherwise undesirable tastes, while providing immediate release of the beneficial pharmaceutical or nutritional supplement upon exposure to the pH levels found in the stomach. The formulations of the present invention comprise: (a) a core of a pharmaceutically active agent or nutritional supplement, as well as diluents, fillers or other inactive ingredients necessary for the formation of the pharmaceutical core; and (b) a single outer polymeric coating layer comprising a prolamine fraction of cereal grain proteins and a low-to-moderate molecular weight hydrophobic plasticizing agent for said prolamine.

Prolamines form the main protein components of cereal grains and flour. Unlike all other proteins, they can be extracted from flour with 80 percent alcohol, but they are insoluble in absolute alcohol and water. The most important prolamines are zein, gliadin, and hordein. In the instant invention, the prolamine fraction is purified from corn or wheat and includes zein or gliadin or mixtures thereof, but preferably is zein (the prolamine fraction of corn) which has been purified to between 86–96% pure zein, most preferentially 92–96% purity. Additionally, the prolamines present in the preferred coating formulation will be present in a solution consisting of 90% food grade ethanol and 10% distilled water at a preferred level (by weight) of between 5% and 20% prolamine.

The hydrophobic plasticizing agent which is preferentially present on a weight basis between 2.5% and 25%, more preferably 5% to 15%, relative to the prolamine fraction, is a water insoluble vegetable oil or wax, and includes, but is not limited to, fatty acids having carbon chain lengths of six to twenty-two (both saturated and unsaturated carbon chains are equally suitable), non-ionic cellulosic polymers (e.g., hydroxypropyl cellulose and/or hydroxyethyl cellulose), and polyvinylpyrrolidone of molecular weight range 30,000 to 400,000 daltons. Most preferred hydrophobic plasticizers are fatty acids having chain lengths six-to-eighteen carbons which are present on a weight basis of between 5 and 15%.

Because the coating composition of the instant invention is designed to rapidly degrade once the product has left the mouth, additional ingredients that lend stability to coating at a pH less than that found in the mouth are not desired. Thus substances such as non-water soluble ethers and esters of cellulose, ethylcellulose, cellulose acetate, cellulose propionate, cellulose acetate butyrate, polyvinyl esters, polyvinyl acetate, and the like, and even organic fillers, such as talc which is also non-water soluble, are not contemplated as ingredients within the scope of the present invention.

The active substances which are believed to be suitable for incorporation in the core of an encapsulated particle in accordance with the present invention are bioactive substances including for example, analgesics, antibiotics, preferably macrolide antibiotics, oncolytics, immunogens, anti-depressants and other physchotherapy drugs, antivirals, drugs to treat HIV compromised individuals and individuals with AIDS, immuno-modulators, antihistamines, decongestants, antiinflammatory agents, vaccines, enzymes, hormones, dietary fiber and other nutrients, antibodies and other pharmaceuticals. The foregoing list is not intended to be inclusive but merely representative of various active compounds both simple and complex that are contemplated in accordance with the present invention. Those active agents having an especially bitter taste, such as macrolide antibiotics, specifically erythromycin and clarithromycin, are particularly suited for the present invention.

The optimum thickness of the coating material is between about 1 and about 35 micrometers. The coating is applied as a single layer. The preferred level of coating consists of from about 5% to about 100% of applied film, where the major constituent is the prolamine fraction of grain protein (with the percent representing the weight of film coating relative to the initial weight of the encapsulated active agent). The most preferred level of coating is between 45 to 75% by weight of coating to weight of the encapsulated active ingredient core.

The preparation of the formulation may be accomplished by a variety of coating techniques known in the art including fluidized bed coating, coacervation, or a combination thereof, and the like, as disclosed in U.S. Pat. No. 4,384,004 to Cea et al. Preferably, fluid bed coating with a rotor insert may be employed to form the initial active agent core, and fluidized bed coating with a Wurster column insert may be employed to apply the coating, as described in U.S. Pat. No. 4,800,087 to Mehta et al. In the fluidized bed procedure, with rotor insert, for preparing a core containing the active agent as employed herein, the active agent or active agent in a matrix is charged as a powder onto a variable speed horizontal rotor disc in an apparatus that creates an upward air current or stream in which the particles have a rotary movement about an at least approximately vertical axis. The particles pass through a zone of finely atomized coating material which causes the passing particles to be coated. Additional solvents can be applied after the application of the coating material to better form particles of the desired size. Finally, rotor speed is increased and fluidization air volume and air temperature are also increased to both form the coated particles and obtain the desired level of dryness. The foregoing method and apparatus are known as a fluidized bed with rotor disc and are set forth in detail in the following U.S. patent, the disclosures of which are incorporated herein by reference: U.S. Pat. Nos. 4,323,312 and Re. 32,307.

In the fluidized bed with Wurster column procedure as applied herein for applying a coating, the active agent cores produced with the fluidized bed with rotor insert described above, or other means, are suspended in an apparatus that creates a strong upward air current or stream in which the particles move. The stream passes through a zone of finely atomized coating material which causes the passing particles to be coated, after which the coated particles move upward through the Wurster column and then travel downward in a fluidized condition countercurrent to a flow of heated fluidized gas whereupon they are dried. The particles may reenter the upward stream for a further coating until the desired weight ratio of coating to active core has been obtained. The foregoing method and apparatus are known as the Wurster Process and are set forth in detail in the following U.S. Patents, the disclosures of which are incorporated herein by reference: U.S. Pat. Nos. 3,089,824; 3,117,027; 3,196,827; 3,241,520; and 3,253,944.

The preferred method for preparing the pharmaceutical or nutritional core is to comix the active agent with a portion of inactive binder consisting of polyvinylpyrrolidone (such as Povidone™ made by the International Speciality Chemicals Corporation) having a molecular weight range of 30,000 to 400,000 on a weight to weight basis of 5% to 65% of the active ingredient. Alternative granulating agents capable of assisting the formation of a particle containing the active ingredient include hydroxypropylcellulose (such as Methocel™, Dow Chemical Corporation), pregelatinized starch, (such as obtained from Colorcon, Inc.) or any other material suitable for use as a binding agent for the formation of particles capable of being utilized as pharmaceutically or nutritionally active core material. After dry blending, a sufficient portion of water or food grade alcohol is added to the dry blend to yield a wet granulation mixture. This material may be either oven-dried under mild heat or dried in a fluidized bed air-drying system, which is capable of performing the task of drying in a more efficient, less time consuming fashion. The particles are then dried to a specific level of dryness (based on weight loss measurements) and milled to produce a small particle size range. These particles may then be sieved to collect the fraction of particles of a particular size range for subsequent coating. Alternate methods for preparing particles are equally useful at creating particles of a suitable size range.

Following production of the particles of the active agent having suitable size, these particles are then coated or encapsulated with the prolamine coating material. The prolamine coating materials are prepared as a solution capable of being uniformly atomized. The solubility of zein requires a solvent containing both polar and non-polar groups in the proper ratio. The proper ratio of polar and non-polar groups can be obtained with single solvents or two or more solvent mixtures. Examples of suitable single solvents are acetic acid, lactic acid, propionic acid, and propylene glycol. The aqueous alcohols are preferred as solvents in many applications. Examples of suitable alcohol/water systems are methanol/water, ethanol/water, isopropanol/water, and n-butanol/water. To obtain complete solubility above the cloud point, the ratio of alcohol to water varies for each alcohol chosen and mixed solvent final temperature. If desired, other ingredients such as plasticizers or hydrophobic substances may be added to improve the properties of the final coating. Suitable plasticizers include triethylene glycol, propylene glycol, oleic acid, lactic acid acetamide, ethylene glycol monooleate, glycerin, glyceryl monostearate, dibutyl tartrate, and tricresyl phosphate. Suitable hydrophobic substances include vegetable and animal fats, either unhydrogenated, hydrogenated, or partially hydrogenated, fatty acids, with representative materials comprising palm oil, palm kernel oil, soybean oil, rapeseed oil, rice bran oil, sunflower oil, safflower oil, coconut oil, castor oil, MCT oil, also known as glycerine ester of C6–C20 fatty acids derived from coconut oil, and mixtures thereof. Other hydrophobic substances also useful herein may be selected from monoglycerides, distilled mono- and diglycerides, triglycerides, acetylated mono- and diglycerides, triglycerides and mixtures thereof. The plasticizer may be added in known effective amounts within the scope of the invention. In general, amounts of about 5% to about 25% by weight of zein are suitable. The thickness of the single layer coating is easily varied by adjusting the solids concentrations of the prolamine and hydrophobic plasticizer dissolved in the coating solution.

The formulation of the present invention may be incorporated into a variety of pharmaceutical and nutritional products, including pharmaceutical suspensions, pediatric infant formulas, and liquid nutritional supplements.

As used herein and in the claims when a coating component is stated as being as a percent of a particle, it should be understood that the coating component by itself is expressed as a weight percent of the particle. In the examples, all values of the weight percent of coating components were determined by analytical analysis. In addition to the stated weight percent of the coating component contained in the coat, the coating would also contain any specified plasticizer or hydrophobic substance at the weight percent specified in the example.

EXAMPLE 1

A. Preparation of Clarithromycin: Polyvinylpyrrolidone Particles.

To a pharmaceutically active core consisting of 90% clarithromycin and 10% polyvinylpyrrolidone (Povidone, K-30, ISP Corp), a sufficient amount of food grade ethanol was added with mixing to form a wet mass. The wet granulation was then dried in an oven set at between 50° and 60° C. until the loss of drying (hereinafter referred to as LOD) was less than 1%. These particles were then ground to a smaller size and fractionated using a sieve having a 40–80 mesh. The fraction of particles having a size between 177 and 420 micron was collected.

B. Preparation of Zein-coated Clarithromycin: Polyvinylpyrrolidone Particles.

To 4 kg of clarithromycin: polyvinylpyrrolidone particles, prepared as described above, was applied 2.8 kg of solids contained in a coating formulation consisting of zein (93%) and medium chain triglycerides (7%). This coating formula was dispersed in a mixture of 90% food grade ethanol and 10% distilled water to a level of 10.75% solids (prolamine fraction and medium chain triglycerides), in this cosolvent mixture. The coating was performed in a Glatt GPCG-5 bottom spray particle coater with a fluidized bed and a Wurster column. Inlet temperature was maintained between 39° and 45° C., with the exhaust temperature between 26° and 29° C., and the atomization pressure on the spray nozzle was maintained between a range of 26 and 30 pounds per square inch. The flow rate of application of the coating liquid to the particles was maintained in the range of 10 to 15 mL per minute. The thickness of the single layer coating is easily varied by adjusting the solids concentrations of the prolamine and hydrophobic plasticizer dissolved in the coating solution.

EXAMPLE 2

Dissolution of Zein-coated Clarithromycin: Polyvinylpyrrolidone Particles as a Function of pH.

The zein coated clarithromycin: polyvinylpyrrolidone particles, prepared as described in Example 1, were tested using a dissolution apparatus to evaluate the percent of active ingredient released into a 900 mL dissolution bath of pH buffered solution over a two hour period. A dose of 125 mg of clarithromycin activity was used as a representative dose and dissolution was tested at pH 2.0, 5.0 and 6.8. Samples were withdrawn at 30, 60, 90 and 120 minutes. The results, as shown by Table 1, indicate no active agent was released at pH 6.8. Rapid release of the active agent was observed at pH 2.0.

TABLE 1

Dissolution of Zein-coated Clarithromycin: Polyvinylpyrrolidone Particles as a Function of solution pH[1].

| Time (minutes) | Percent (%) Clarithromycin Released | | |
|---|---|---|---|
| | pH 2 | pH 5 | pH 6.8 |
| 30 | 80.8(8.1)[2] | 35.9(22.3) | nd[3] |
| 60 | 90.9(3.0) | 52.9(13.2) | nd |
| 90 | 94.7(4.1) | 62.4(8.5) | nd |
| 120 | 96.3(2.8) | 69.4(11.7) | nd |

[1]Particles coated with 70% weight coating to weight of particle.
[2]Average (± standard deviation); number of determinations in each case = 3.
[3]No detectable release.

EXAMPLE 3

Release of Zein-coated Clarithromycin: Polyvinylpyrrolidone Particles as a Function of Storage Time.

To a solution in which sodium bicarbonate (50 mg/5 mL) was dissolved, 125 mg/5 mL of zein coated clarithromycin activity (accounting for potency of the active agent and the particles), was added, shaken and observed for release of active agent as a function of time. The final pH of this suspension was greater than pH 6.0. Samples were withdrawn, filtered, and measured at 0, 4, 24, 72, and 196 hours. The samples were filtered to remove the suspended particles and the clear filtrate was analyzed for clarithromycin content. The results, as shown in Table 2, below, indicate that very low levels of active drug are released from the zein encapsulated material over prolonged periods of storage time. Even after more than 8-days storage, less than 0.5% of the encapsulated clarithromycin had leaked through the zein coating.

TABLE 2

Release of Zein-coated Clarithromycin: Polyvinylpyrrolidone Particles as a Function of Storage Time.

| Time (hours) | Concentration (micrograms/mL) | Percent (%) Release |
|---|---|---|
| 0 | 20 | 0.08 |
| 4 | 60 | 0.24 |
| 24 | 99 | 0.40 |
| 72 | 118 | 0.47 |
| 196 | 102 | 0.41 |

Thus, this example shows that a suspension, having a final pH greater than about pH 6.0, containing particles having an active substance in a core coated with a single layer of a mixture consisting of prolamine and hydrophobic plasticizer has been reduced to practice, with minimal leakage of the active substance into the suspending medium.

EXAMPLE 4

Formulation of Zein Coated Clarithromycin.

Zein coated clarithromycin, comprising 70% coating was formulated as follows:

| Ingredient | Amount per dose (5 mL) |
|---|---|
| Coated clarithromycin | 260 mg (125 mg activity) |
| Sucrose | 3000 mg |
| Xanthan Gum | 7.5 mg |
| Silica Gel | 10.0 mg |
| Potassium Sorbate | 20.0 mg |
| Bubble Gum Flavor | 14.0 mg |
| Sodium Bicarbonate | 50.0 mg |
| Totals: | 3361.5 mg per 5 mL final volume. |

The purpose of this example is to demonstrate that the particles in accordance with the invention may be dispersed in a liquid medium to yield a taste masking suspension of the active substance. As used herein and in the claims, a "liquid suspension" is understood to be an oil based liquid, aqueous based liquid, or a liquid that has a base which is a combination of water and oil. As used herein and in the claims, a "liquid" is understood to mean a state of matter in which the molecules are relatively free to change their positions with respect to each other but are restricted by cohesive forces to maintain a relatively fixed volume.

EXAMPLE 5

Bioavailability of Zein-coated Clarithromycin

The bioavailability of zein-coated clarithromycin, formulated as described in Example 4, was conducted in a beagle dog model using a single cross-over design. The study compared single dose immediate release containing 125 mg of clarithromycin activity to the zein encapsulated clarithromycin particles prepared as described in Example 1, and formulated as described in Example 4. The release of clarithromycin was demonstrated by a cross over comparison of the bioavailability of the formula in a beagle dog model compared to a tablet reference containing the same amount of clarithromycin. The cross over design allowed the same dogs to receive both the zein coated clarithromycin suspension as well as the clarithromycin reference tablet containing the same amount of clarithromycin (125 mg of clarithromycin activity). The results, illustrated in FIG. 1, demonstrate that the zein-coated clarithromycin suspension did not release the clarithromycin in suspension (as shown by a representative suspension in Example 3, Table 2), but rapidly released the active drug in the low pH conditions of the gastrointestinal tract of the dog. As illustrated in FIG. 1 the level of clarithromycin in the plasma of the dogs, indicated that equivalent adsorption of the zein- encapsulated clarithromycin and of clarithromycin contained in the uncoated rapid release tablet occurred.

EXAMPLE 6

Flavor Evaluation of Zein-coated Clarithromycin

The concept that the taste masking of the unpleasant taste of an active substance suspended in a liquid is primarily achieved by the exterior coating of the active substance is supported by studies performed on the macrolide antibiotic, clarithromycin.

Comparative flavor evaluation, noting characteristics of bitterness of the zein coated clarithromycin particles suspended in solution was conducted. The formulation used was that described in Example 4, and was compared with uncoated clarithromycin in solution as a standard reference for the level of bitterness observed for the various samples. The study was conducted using a panel of specially trained flavor and taste specialists. This taste panel standardized their palate with the use of reference samples which were, in this case, solutions containing varying amounts of uncoated clarithromycin, herein after also referred to as "standards". The study consists of swirling a dose of the solution or suspended formulation in the mouth and then ranking bitterness, relative to the standards, as a function of time after tasting it. The period of time after tasting is evaluated in the event that particles remain or get lodged in the oral cavity before being removed by salivary secretions.

Figure 2:
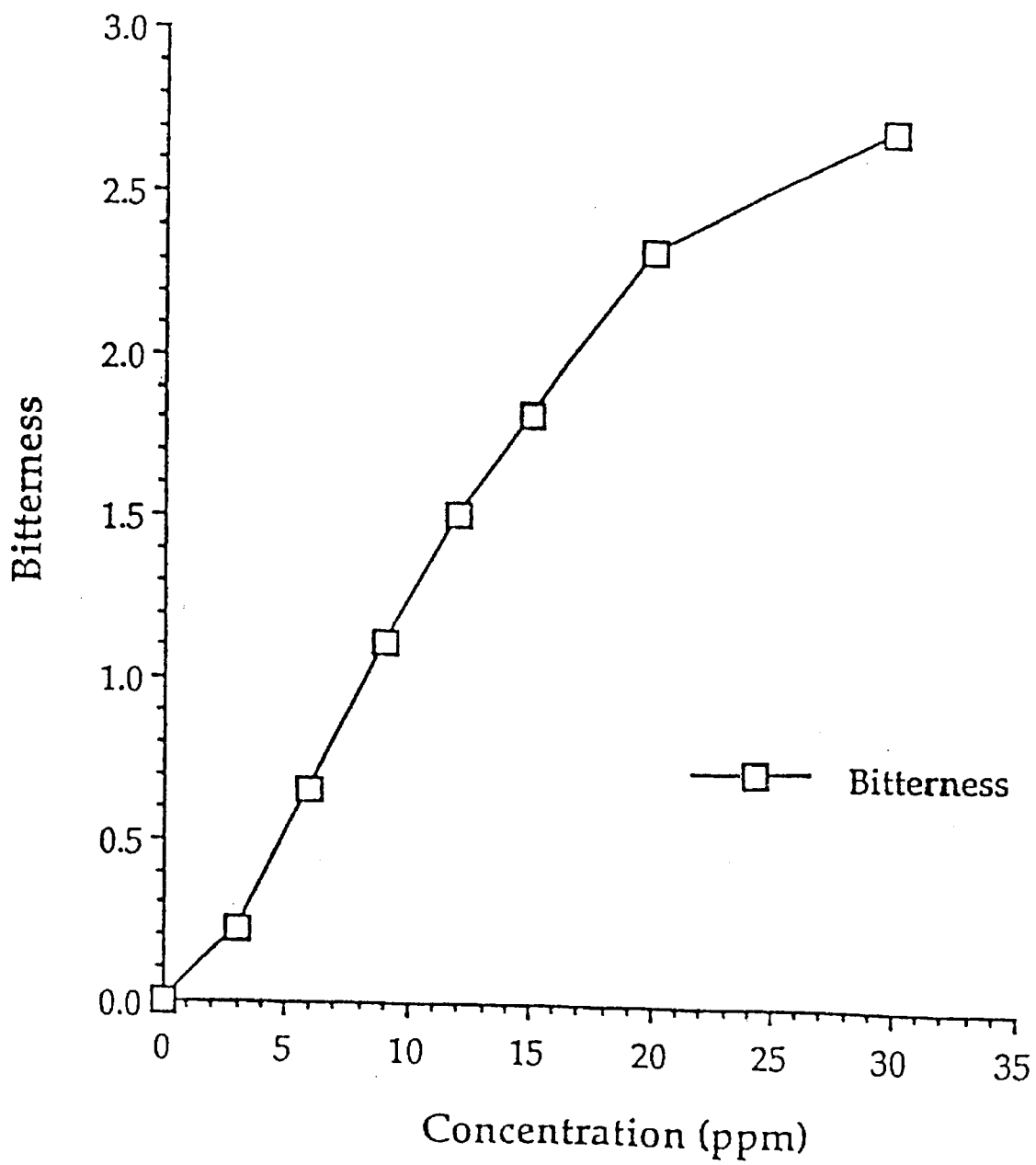
FIG. 2 is a graph of the bitterness (on a scale of 0 to 3, where 0 represents no bitterness and 3 represents a strong bitterness) observed for a clarithromycin concentration in solution.
Figure 3:
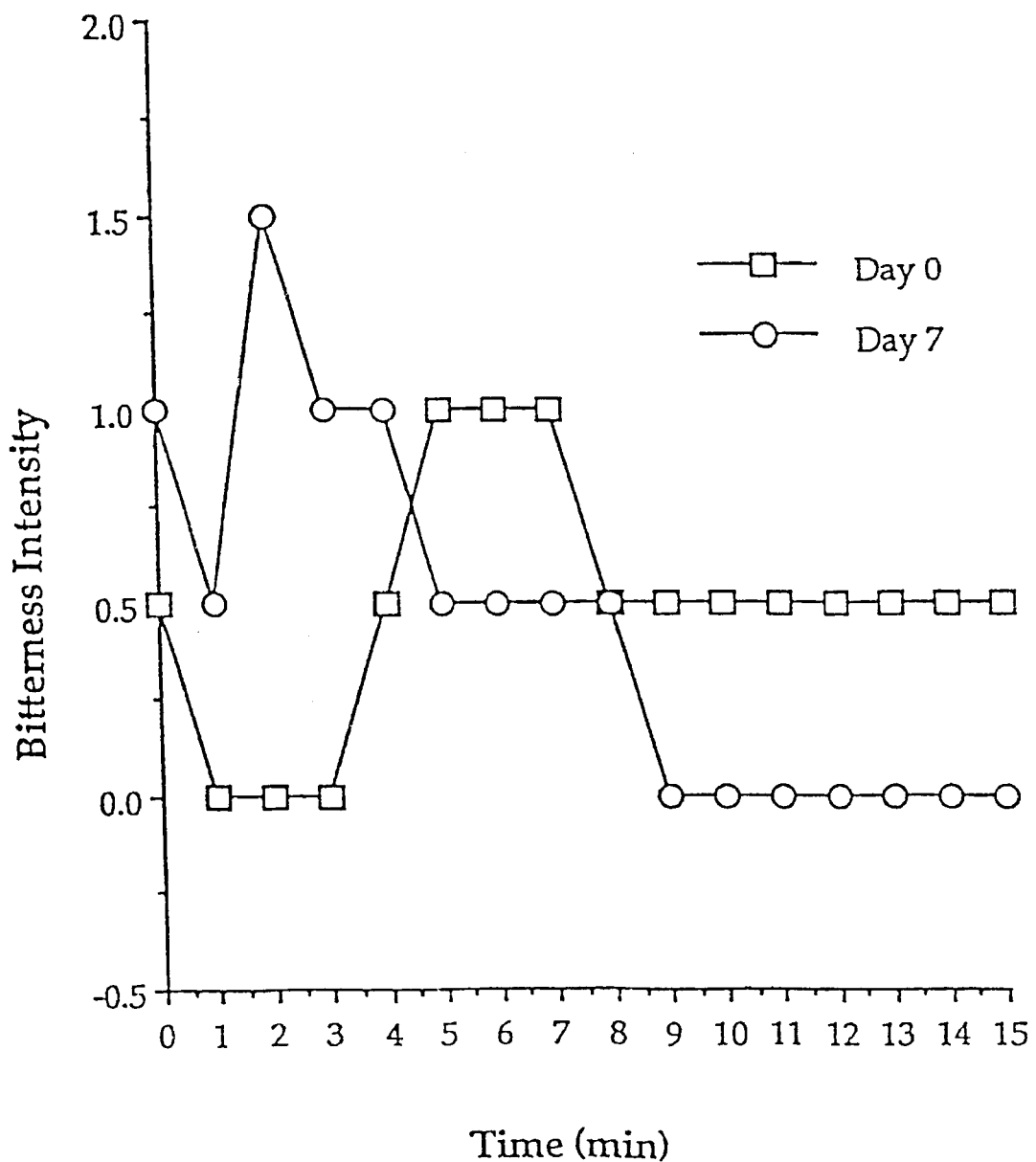
FIG. 3 is a graph of the bitterness as a function of time after tasting, observed for the formulation of clarithromycin particles coated with a single layer of zein and suspended in an aqueous environment for both an initially-prepared suspension (Day 0) and a suspension which was prepared and allowed to stand for seven days (Day 7). This comparison illustrates the taste masking stability of the zein coated suspension.

The bitterness dose response for the uncoated clarithromycin in solution can be seen in FIG. 2 and the corresponding level of response for the zein coated clarithromycin suspension is shown in FIG. 3, as a function of time after tasting. FIG. 2 illustrates that a solution containing 3 parts per million (ppm) of uncoated clarithromycin yields a bitterness index of 0.2, whereas a solution containing 10 ppm of uncoated clarithromycin has bitterness index of about 1.1, and a solution containing 20 ppm has a bitterness value of 2.5, etc. FIG. 3 shows that immediately after production (Day 0), the zein coated clarithromycin suspension exhibits a bitterness index below 1.0 corresponding to a free uncoated clarithromycin concentration of less than 10 ppm. FIG. 3 further illustrates that even after seven days storage (Day 7), the zein coated clarithromycin suspension exhibits a bitterness index below 1.5. This value corresponds to about 15 ppm of uncoated clarithromycin as shown in FIG. 2. Thus, FIG. 3 shows even after seven days of storage of the zein coated clarithromycin suspension, that the levels of free clarithromycin available for interaction with the taste buds is below 15 ppm. This demonstrates the ability of the zein coating to effectively mask the taste of a very bitter pharmaceutically active agent such as clarithromycin. FIG. 3 also demonstrates the ability of the zein coating to produce a stable formulation which releases not more than 15 ppm of clarithromycin after seven days of storage of the zein coated clarithromycin suspension.

By way of further explanation, it should be noted that the tested preparation contained 125 mg of clarithromycin per 5 ml of suspension (see Example 4). This corresponds to well over 185,000 ppm of clarithromycin. Thus FIG. 3 illustrates that substantially less than 0.01% of the available clarithromycin is released from the zein coated clarithromycin-polyvinylpyrrolidone particles of Example 4 even after seven days storage.

EXAMPLE 7

Comparative

A. Preparation of Clarithromycin Pellets.

To a pharmaceutically active core consisting of 100% clarithromycin, a sufficient amount of food grade ethanol was added with mixing to form a wet mass. The wet granulation was then dried in an oven set between 50° and 60° C. until the loss of drying (LOD) was less than 1%. These particles were then grounded to a smaller size, sieved through a 40–80 mesh and the fraction of particles in the size range between 177 and 420 microns was collected.

B. Preparation of Zein/Stearic Acid/Talc-Coated Clarithromycin.

A zein based coating formula was prepared to coat the clarithromycin particles produced above. The coating solution was made by first adding 1890 grams of 200 proof grade ethanol to 810 grams of distilled water. As this solution was being mixed, 165 grams of zein, 120 grams of stearic acid, and 15 grams of talc were slowly added in succession. The resultant solution was mixed until the solids were in solution. After the solids were in solution, the clarithromycin particles, prepared as described above, were coated. The coating was performed in a Glatt GPCG-5 bottom spray particle coater with a fluidized bed and a Wurster column. Inlet temperature was maintained between 39° and 45° C., with the exhaust temperature between 26° and 29° C., and the atomization pressure on the spray nozzle was maintained between a range of 26 to 30 pounds per square inch. The flow rate of application of coating liquid to the particles was maintained in the range of 10 to 15 mL per minute. The clarithromycin particles were coated with various amounts of the above coating. Specifically, the particles had coating of 20, 40 and 60 percent (w/w) based on the weight of the clarithromycin particles. The thickness of the single layer coating is easily varied by adjusting the solids concentrations of the prolamine and hydrophobic plasticizer dissolved in the coating solution.

C. Dissolution of Zein Coated Clarithromycin as a Function of Time in pH 2 Buffer.

The zein coated clarithromycin particles, prepared as described above, were tested using a dissolution apparatus to evaluate the percent of active ingredient released into a 900 mL dissolution bath of pH-buffered solution at a temperature of 40° C. A dose of 125 mg of clarithromycin activity was used as a representative dose and dissolution was tested at pH 2.0 and 6.0. samples were withdrawn at 60, 120, 240, and 360 minutes. The results, as shown by Tables 3, 4, and 5 below, indicate rapid release of active drug for all coating concentrations at pH 2.0. Increasingly, proportionally to the coating amount, slow release of the active drug was observed at pH 6.0.

TABLE 3

| | Level of Coating: 20% | |
|---|---|---|
| | Percent of Clarithromycin Released | |
| Time (minutes) | pH 2.0 | pH 6.0 |
| 60 | 97 | 38 |
| 120 | 100 | 55 |

TABLE 3-continued

Level of Coating: 20%

| | Percent of Clarithromycin Released | |
|---|---|---|
| Time (minutes) | pH 2.0 | pH 6.0 |
| 240 | 100 | 75 |
| 360 | 100 | 85 |

TABLE 4

Level of Coating: 40%

| | Percent of Clarithromycin Released | |
|---|---|---|
| Time (minutes) | pH 2.0 | pH 6.0 |
| 60 | 98 | 21 |
| 120 | 100 | 30 |
| 240 | 100 | 42 |
| 360 | 100 | 57 |

TABLE 5

Level of Coating: 60%

| | Percent of Clarithromycin Released | |
|---|---|---|
| Time (minutes) | pH 2.0 | pH 6.0 |
| 60 | 100 | 11 |
| 120 | 100 | 16 |
| 240 | 100 | 24 |
| 360 | 100 | 31 |

As shown in Table 1, for a 70% coating, no detectable release of active substance occurred at pH 6.8. This example shows that a suspension containing particles having an active substance in a core coated with a single layer of a mixture consisting of prolamine and hydrophobic plasticizer and exhibiting minimal leakage of the active substance into the suspension medium has been reduced to practice.

Although the invention has been exemplified in specific modifications, the details are not to be construed as limitations, for it will be apparent that various equivalent, changes and modifications may be employed without departing from the spirit and scope thereof, it being understood that such equivalent embodiments are intended to be included therein.

What is claimed is:

1. An orally consumable liquid comprising an active substance in particle form contained in a liquid suspension having a pH greater than about 6.0, each particle comprising a core containing a physiologically active agent, said core being encapsulated by a single coating layer of from about 1 to about 35 micrometers thick wherein the weight ratio of said active substance to said coating layer is from 20:1 to 1:1, said coating consisting essentially of a prolamine and at least one material selected from the group consisting of plasticizers and hydrophobic substances, the taste of the active agent being masked by said coating layer substantially preventing the dispersion of the active substance into the suspension while being readily disintergrated by human gastric juices such that the active agent is immediately released therein.

2. The orally consumable liquid of claim 1 wherein said prolamine comprises an amount of from about 30% to about 70% by weight of the sum of the weights of said active agent and said single coating layer, and wherein the ratio of prolamine to said plasticizers and hydrophobic substances in said coating layer is from 40:1 to 4:1.

3. The orally consumable liquid of claim 2 wherein said prolamine comprises an amount of from about 40% to about 60% by weight of the sum of the weights of said active agent and said single coating layer.

4. The orally consumable liquid of claim 2, wherein said ratio of prolamine to hydrophobic plasticizers is from 20:1 to 20:3.

5. The orally consumable liquid of claim 1, wherein said hydrophobic plasticizing agent is a water-insoluble vegetable source oil or wax having a fatty acid chain length of about six to twenty-two carbon atoms.

6. The orally consumable liquid of claim 1 wherein the active substance is selected from the group consisting of analgesics, antibiotics, anti-depressants, antivirals, antibodies, immunomodulators, oncolytics, immunogens, hormones, vaccines, enzymes and nutritional supplements.

7. The orally consumable liquid of claim 6 wherein said antibiotic is selected from the group consisting of clarithromycin and erythromycin.

8. The orally consumable liquid of claim 6 wherein said nutritional supplements are selected from the group consisting of proteins, amino acids, vitamins and dietary fiber.

9. The orally consumable liquid of any one of claims 1 through 5 and 6 wherein the prolamine is selected from the group consisting of zein, gliadin or hordein.

10. The orally consumable liquid of any one of claims 1 through 5 and 6 wherein the prolamine is zein.

* * * * *